(12) United States Patent
Karmali (10) Patent No.: US 8,034,823 B2
(45) Date of Patent: Oct. 11, 2011

(54) METHOD OF INCREASING DRUG ORAL BIOAVAILABILITY AND COMPOSITIONS OF LESS TOXIC OROTATE SALTS

(75) Inventor: Rashida A. Karmali, New York, NY (US)

(73) Assignee: Savvipharm Inc, New York, NY (US)

( * ) Notice: Subject to any disclaimer, the term of this patent is extended or adjusted under 35 U.S.C. 154(b) by 362 days.

(21) Appl. No.: 11/063,943

(22) Filed: Feb. 22, 2005

(65) Prior Publication Data

US 2006/0189640 A1 Aug. 24, 2006

(51) Int. Cl.
*A61K 31/505* (2006.01)

(52) U.S. Cl. .................................................. 514/274

(58) Field of Classification Search .................. 514/274, 514/255, 359; 544/310
See application file for complete search history.

(56) References Cited

U.S. PATENT DOCUMENTS

| | | | |
|---|---|---|---|
| 3,118,890 A * | 1/1964 | Ferguson, Jr. | 544/314 |
| 3,271,398 A * | 9/1966 | Haraoka et al. | 544/310 |
| 4,061,741 A * | 12/1977 | Wawretschek et al. | 514/161 |
| 5,004,756 A | 4/1991 | Ogawa et al. | |
| 5,039,527 A | 8/1991 | Tabibi et al. | |
| 5,461,037 A | 10/1995 | Cotter | |
| 5,710,145 A * | 1/1998 | Engel et al. | 514/183 |
| 5,861,406 A | 1/1999 | Wehrmann | |
| 5,912,346 A * | 6/1999 | Wehrmann | 544/310 |
| 6,184,227 B1 * | 2/2001 | Karmali | 514/274 |
| 6,239,137 B1 * | 5/2001 | Karmali et al. | 514/274 |
| 6,258,795 B1 * | 7/2001 | von Borstel et al. | 514/49 |
| 6,472,378 B2 * | 10/2002 | von Borstel | 514/50 |
| 6,838,090 B2 * | 1/2005 | Tabibi et al. | 424/450 |
| 6,858,650 B1 * | 2/2005 | Meese | 514/530 |
| 2005/0209247 A1 * | 9/2005 | Cai et al. | 514/253.07 |

FOREIGN PATENT DOCUMENTS

BE 645 218 A * 7/1964
DE 2612780 * 9/1977

OTHER PUBLICATIONS

Malingre et al., Coadministration of cyclosporine strongly enhances the oral bioavailability of docetaxel, J. Clinical Oncol. vol. 19(4) pp. 1160-1166, 2001.*
Merriam-Webster's Collegiate Dictionary, Tenth Edition (1996), Springfiled, Massachusetts, p. 66.*
Sobek et al. Arzneimittel-Forschung, 1967, vol. 17, No. 6, pp. 711-714 (Abstract attached).*
Gould et al. International Journal of Pharmaceutics, 1986, vol. 33, pp. 201-217.*
English Abstract of DE 2612780, STN Accession No. 1978:11920.*
Bauer , KS et al, Clin Cancer Res 5:2324-2329 (1999).
Desai et al Cancer Chemother Pharmacol 54: 377-384 (2004).
I. Sugiyama et al ,Biochem Biophy Acta 1653:47-59 (2003).
J. Malingre et al, J Clin Oncol 19: 1160-1166 (2001).
K. Purow et al, Cancer Inv 22: 577-587 (2004).
L. Maccoss et a,l Science 303: 1810-1813 (204).
M. El Hag et al, In Vivo 1: 309-312 (1987).
N. Kohn et al, Cancer Res 52: 3208-3212 (1992).
Bauer et al, J. Pharm Exp Therap 292: 31-37 (2000).

* cited by examiner

Primary Examiner — James Anderson
(74) Attorney, Agent, or Firm — Rashida A. Karmali (57) ABSTRACT

The present invention relates generally to the method of increasing the oral bioavailability, reducing chemotherapy induced toxicity and side effects, and improving the effectiveness of pharmaceutical agents that are poorly absorbed from the gastrointestinal tract. Specifically, the invention relates to poorly absorbed pharmaceutical drugs and converting them to orotate salts. The orotate salts of the drugs can be dosed at lower doses to provide the efficacy benefits of a higher dose, while reducing the drugs' toxic effects at lower doses. Additionally, the orotate salts of pharmaceutical agents have better clearance and reduce the potential for drug-induced hepatic toxicity. Therefore, an especially useful formulation of the orotate salt of the pharmaceutical agent can provide rapid and consistent action using a lower dose while reducing drug interactions and side-effects.

29 Claims, 6 Drawing Sheets

| CAI | | | | |
|---|---|---|---|---|
| PO Dose = 100 mg/kg | | | | |
| Time (hr) | Concentration (ng/kg) | | | Mean |
| | Animal # | | | |
| | 1 | 2 | 3 | |
| 0 | 0 | 0 | 0 | 0 |
| 0.30 | 202 | 167 | 43 | 137 |
| 1 | 463 | 393 | 286 | 381 |
| 2 | 832 | 977 | 579 | 796 |
| 4 | 1435 | 2240 | 1115 | 1597 |
| 16 | 1220 | 3365 | 3215 | 2600 |
| 48 | 960 | 714 | 847 | 840 |
| Pharmacokinetic Estimates | | | | |
| Half-life (hr) | | | | 19.630 |
| $C_{max}$ (ng/mL) | | | | 2600.00 |
| $T_{max}$ (hr) | | | | 16.0 |
| $AUC_{0-T}$ (hr·ng/mL) | | | | 83408.2 |
| Vd (area)/kg (ml/kg) | | | | 3434.8 |
| CL (area)/kg (ml/hr/kg) | | | | 121.3 |

| CAI Orotate | | | | |
|---|---|---|---|---|
| PO Dose = 137 mg/kg | | | | |
| Time (hr) | Concentration (ng/kg) | | | Mean |
| | Animal # | | | |
| | 1 | 2 | 3 | |
| 0 | 0 | 0 | 0 | 0 |
| 0.30 | 188 | 1405 | 1545 | 1046 |
| 1 | 322 | 2150 | 1830 | 1434 |
| 2 | 806 | 2610 | 3170 | 2195 |
| 4 | 945 | 3050 | 4620 | 2872 |
| 16 | 3360 | 3870 | 5960 | 4397 |
| 48 | 959 | 704 | 2125 | 1263 |
| Pharmacokinetic Estimates | | | | |
| Half-life (hr) | | | | 17.77 |
| $C_{max}$ (ng/mL) | | | | 4397 |
| $T_{max}$ (hr) | | | | 16.0 |
| $AUC_{0-T}$ (hr·ng/mL) | | | | 142066 |
| Vd (area)/kg (ml/kg) | | | | 20139.5 |
| CL (area)/kg (ml/hr/kg) | | | | 785.3 |

FIG. 6

Orotate

US 8,034,823 B2

METHOD OF INCREASING DRUG ORAL BIOAVAILABILITY AND COMPOSITIONS OF LESS TOXIC OROTATE SALTS

1. FIELD OF INVENTION

The present invention relates generally to the method of increasing the oral bioavailability of pharmaceutical agents that are poorly absorbed from the gastrointestinal tract, and to methods of improved treatment of patients through the oral administration of such agents. In particular, the invention relates to poorly absorbed pharmaceutical drugs and converting them to orotate salts to enhance the drugs' oral bioavailability. Thus, the orotate salts of the drugs can be dosed at lower doses to provide the efficacy benefits of a higher dose, while reducing the drugs' toxic effects at lower doses and reduce acute and delayed-phase chemotherapy-induced nausea and vomiting. Additionally, the orotate salts have a higher clearance rate, i.e., the fraction of the drug escaping first pass metabolism is increased. Therefore, an especially useful formulation of the orotate salt of the pharmaceutical agent can provide rapid onset and consistent action using a lower dose and reduce drug interactions and side-effects because of consistent delivery.

2. BACKGROUND TO THE INVENTION

Many pharmacologically active agents cannot be effectively administered by the oral route because of poor systemic absorption from the gastrointestinal tract. Therefore, these agents are generally administered via the intravenous or intramuscular routes. This requires hospitalization or care by a health professional, entailing discomfort, potential trauma to the patient and even added cost. Other pharmacologically active agents may be administered by the oral route, but a combination of poor absorption and/or rapid breakdown during the first pass through the liver, requires large and toxic doses to achieve therapeutic concentrations systemically.

Methods disclosed in the art for increasing gut absorption of drugs focus on the use of solubility and permeation enhancers as promoting agents. But the above methods suffer from numerous drawbacks. The solubility and permeability enhancers are often ineffective for oral administration in the doses required and may interfere with pharmacological activity of the target drug. Some even cause clinical consequences, for example, intravenous administration of quinidine may cause arrhythmias, peripheral vasodilation, upset gastrointestinal function and the like.

Difficulties continue to exist in delivery systems for water-insoluble pharmaceutical agents despite the development of techniques using lipid vesicles and oil-in-water type of emulsions. However, these formulations require presence of solvents such as dimethyl sulfoxide or polyethylene glycol that cause physical instability in the formulation. Ogawa et al., U.S. Pat. No. 5,004,756; Tabibi et al., U.S. Pat. No. 5,039,527; and Carter, U.S. Pat. No. 5,461,037.

U.S. Pat. No. 6,838,090 claims a vesicular drug delivery system which comprises a drug solution comprising a water-insoluble drug, dissolved in a pharmaceutically acceptable water miscible organic solvent, and a surfactant suspension comprising water and 0.5% to 10% (w/v) of a surfactant wherein the surfactant forms vesicles having an average particle size from 50 nm to 200 nm, wherein the drug solution and surfactant suspension are stored and transported separately, and combined prior to use. The water-insoluble drugs included antihypertension drugs, antibiotics, anticancer or antitumor drugs, and specifically selected from the group consisting of 17-allylaminogeldanamycin and carboxyamidotriazole (CAI). The water-miscible organic solvent was selected from the group consisting of dimethyl formamide, ethanol, glycerine, propylene glycol, polyethylene glycol, dimethyl sulfoxide and dimethyl acetamide.

With the advent of nanotechnology, drug delivery systems have improved but the side effects and toxicity profiles of the drugs have remained unchanged.

It is well known that a series of membrane-bound P-glycoproteins function as energy-dependent transport or efflux pumps to prevent certain pharmaceutical compounds from traversing the mucosal cells of the small intestine and, therefore from being absorbed into the systemic circulation. A number of non-cytotoxic pharmacological agents have been shown to inhibit P-glycoprotein, including cyclosporine, verapamil, tamoxifen, quinidine and phenothiazines, among others. Many of these studies were conducted to achieve greater accumulation of cytotoxic drugs inside tumor cells, for example, the effects of cyclosporine were studied on the pharmacokinetics and toxicities of paclitaxel, doxorubicin and etoposide (Sugiyama et al Biochem Biophys Acta 1653: 47-59 (2003); Malingre et al., J. Clin Oncol 19: 1160-1166 (2001)). All of these drugs are anti-cancer agents known to be subject to multidrug resistance (MDR). These studies indicated that concomitant administration of cyclosporine suppressed the MDR action of P-glycoprotein and resulted in larger intracellular accumulations of the therapeutic agents.

Another approach taken to modulate the pharmacological profile of a drug is to inhibit or prevent its metabolism. Carboxyamidotraiazole (CAI) is a novel neoplastic agent in clinical development with limited oral bioavailability (Bauer et al, Clinical Cancer Research 5:2324-2329, (1999). Since in vitro, ketoconazole has been demonstrated to inhibit CYP3A4 mediated metabolism of CAI, a phase I trial in forty seven patients was undertaken in which CAI and ketoconazole were co-administered. There was an increase in the area under curve (AUC) and Cmax with a decrease in CAI clearance compared to the control. However, the toxicity profile of CAI was not altered (Desai et al, Cancer Chemotherapy Pharmacology 54: 377-384, (2004).

Carboxyamidotriazole (CAI) is currently under development for clinical use as an antitumor agent based on its antiangiogenic, antiproliferative and antimetastatic effects Kohn et al Cancer Res 52: 3208-3212, (1992); Bauer et al J. Pharm Exp Ther 292: 31-37 (2000) and Purow et al, Cancer Investigation 22: 577-587, (2004).

U.S. Pat. No. 5,861,406 issued on Jan. 19, 1999 and U.S. Pat. No. 5,912,346 issued on Jul. 15, 1999, describe treatment and prevention of neoplasms with salts of aminoimizazole carboxamide and CAI triazole. Specifically, an orotate salt of CAI compared with CAI, was found to have improved antitumor effect in the Dunning rat model for prostate cancer. The mechanism of action for the enhancement in antitumor activity of CAI orotate was not described but was suggested to involve an alteration in cyclic nucleotide activity in the liver.

At most pharmaceutical companies, while many technologies such as combinatorial chemistry, nanotechnology, rapid analog synthesis, automated synthesis open access liquid chromatography mass spectrometry, and high-speed automated high-performance liquid chromatography are now affecting medicinal chemistry, their main effect has been to shorten the cycle time of synthetic operations. One of the most difficult properties to build into a newly discovered lead molecule is the desired pharmacokinetic profile, particularly in the case of orally dosed compounds. "Most experienced medicinal chemists would prefer to start in a structural series that has inherently good pharmacokinetic properties, albeit with poor potency on the target receptor, and then set about improving the potency on the target, rather than working in the other direction", "Organic Chemistry in Drug Discovery, Drug Discovery", Science 303: 1810-1813 (2004) by Malcolm MacCoss and Thomas A. Baillie, Merck Research Laboratories, Rahway, N.J.

The present invention describes novel effects of orotate salts of pharmaceutical agents including CAI, on oral bioavailability of the agent. We have now, surprisingly found that oral administration of orotate salts of pharmaceutical agents, for example, CAI orotate, increases the bioavailability of charged CAI compared with the administration directly of the chemical equivalent of CAI. The CAI orotate salt has a better absorption profile which may be related to less side effects such as symptoms of emesis recorded, compared with CAI. These effects are expected to apply to other orotate salts of pharmaceutical agents in use.

The present invention also demonstrates the advantage of administering a drug as an orotate salt on reducing the drug's toxicity. The orotate salts of pharmaceutical agents have better clearance, that is, the fraction of the drug escaping first pass metabolism is increased thus reducing the potential for hepatic toxicity. Therefore, the higher and more consistent bioavailability of a drug when administered as orotate salt of drug orally and/or intravenously, improves the effectiveness and also attenuates the potential effects of any drug side effects and interactions. Medicinal chemists and organic chemists have heretofore, overlooked the unique design of drugs of the present invention.

3. SUMMARY OF THE INVENTION

The present invention provides a method for increasing the bioavailability of a pharmaceutical agent by converting it to an orotate salt. The methods of the invention can be used in general, to increase drug bioavailability in human and other mammals.

The methods of the invention can also be used to achieve consistency in delivery of the pharmacological drugs when administered as orotate salts.

The methods of the invention can be used to reduce multi-drug resistance when the pharmacological drugs are administered as orotate salts.

The methods of the invention can also be used to reduce toxicity of pharmaceutical agents when administered as orotate salts.

The methods of the invention can also be used to improve the clearance of pharmaceutical agents during first pass when administered as orotate salts through the organs of extraction.

The methods of the invention can further be used to reduce drug interactions and side effects when the pharmacological drugs are administered as orotate salts.

It is also the object of the invention to synthesize orotate salts of other water-insoluble antitumor drugs, including but not limited to, paclitaxel, adriamycin, epirubicin, cyclophosphamide, doxorubicin, fluorouracil, taxol, taxotere, vinblastine, methotrexate, tamoxifen, among others, thereby making the orotate derivatives suitable for oral administration.

It is also the object of the invention to systhesize orotate salts of water-insoluble drugs having an ionizable center, to improve the drug's oral bioavailability and efficacy, and reduce the drug-related toxicity and side effects. The compound or drug can be for example, but is not limited to the following classes: acetanilide, aminoacridine, aminoimidazole, aminoquinoline, anilide, anthracycline antibiotic, anti-estrogen, benzazepine, benzhydryl compound, benzodiazpine, benzofuran, cannabinoid, cephalosporine, colchicines, cyclic peptide, dibenzazepine, digitalis glycoside, dihydropyridine, epiphodophyllotoxin, ergoline, ergot alkaloid, imidazole, isoquinoline, macrolide, naphthalene, nitrogen mustard, opioid, oxazine, oxazole, paclitaxel, phenothiazine, phenylalkamine, phenylpiperidine, piperazine, piperidine, polycyclic aromatic hydrocarbon, pyridine, pyridine, pyrimidine, pyrrolidine, pyrrolidinone, quinazoline, quinoline, quinine, rauwolfa alkaloid, retinoid, salicylate, steroid, stilbene, sulfone, sulfonylurea, triazole, tropane or vinca alkaloid.

5. DETAILED DESCRIPTION OF THE INVENTION

The present invention relates generally to the method of increasing the oral bioavailability of pharmaceutical agents that are poorly absorbed from the gastrointestinal tract, and to methods of improved treatment of patients through the oral administration of such agents. In particular, the invention relates to poorly absorbed pharmaceutical drugs and converting them to orotate salts to enhance the drugs' oral bioavailability. Thus, the orotate salts of the drugs can be dosed at lower doses to provide the efficacy benefits of a higher dose, while reducing the drugs' toxic effects at lower doses. Additionally, the orotate salts of pharmaceutical agents have better clearance, that is, the fraction of the drug escaping first pass metabolism is increased, thus reducing the potential for hepatic toxicity. Therefore, an especially useful formulation of the orotate salt of the pharmaceutical agent can provide rapid onset and consistent action using a lower dose and reduce drug interactions and side-effects because of consistent delivery. The present invention provides methods to synthesize orotate salts of water-insoluble drugs having an ionizable center, to improve the drugs' oral bioavailability and efficacy.

The absorption of drugs via the oral route is a subject of intense investigation in the pharmaceutical industry since good bioavailability implies that the drug is able to reach the systemic circulation by mouth. Oral absorption is affected by both the drug properties and the physiology of the gastrointestinal tract, including drug dissolution from the dosage form, the manner in which the drug interacts with the aqueous environment and membrane, permeation across the membrane, and irreversible removal by first-pass organs such as the intestine, liver and lung. Some pharmaceutical agents that exhibit low-solubility show poor bioavailability or irregular absorption, the degree of irregularity being affected by factors such as dose level, fed state of the patient, and physicochemical properties of the drug.

Figure 1:
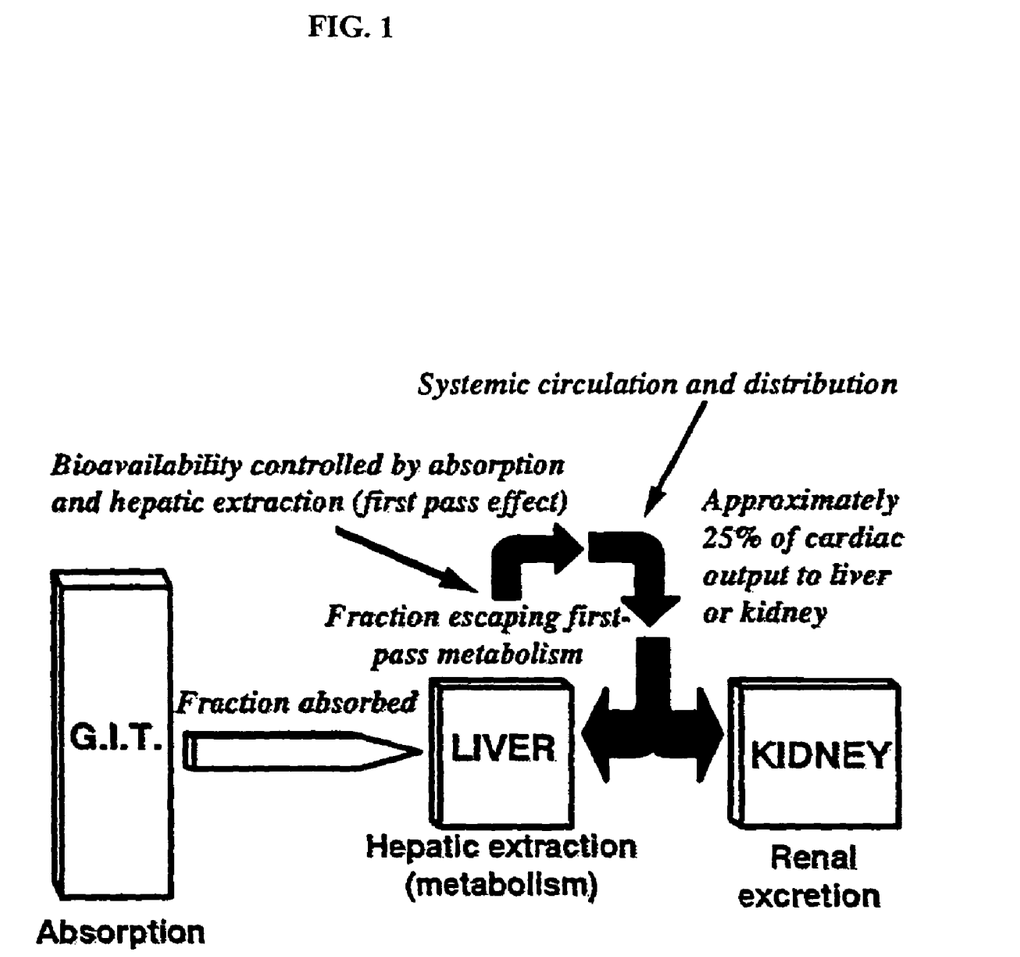
FIG. 1 illustrates the disposition of a drug after oral administration.

The majority of drug absorption occurs at the small intestine because of the large surface area since the presence of the villi and microvilli increases the absorptive area manifold. The duodenum and jejunum possess the greatest surface areas due to the highest concentration of villi and microvilli in these regions compared with that of the ileum. The circulation of the intestine is unique in that the intestine is the anterior or portal tissue that regulates the flow of substrates to the liver. The intestinal venous blood constitutes about 75% of the blood supply to the liver. Therefore, for drugs that are highly cleared by the intestine, the contribution of the liver, kidney or lung to drug metabolism will become reduced. Conversely, for drugs that are poorly extracted by the intestine, the substrate is able to reach the next organs, the liver and the lung for removal. Therefore, the concentration of drug entering the intestine and the intestinal flow rate alter the rate of drug delivery and affect the rates of intestinal and clearance through hepatic first-pass metabolism. FIG. 1 is a schematic representation of the disposition of a drug after oral administration.

"Drug bioavailability" is defined here as the amount of drug systemically available over time. The present invention increases drug bioavailability of pharmaceutical agents by converting them into orotate salts. This may be achieved by altering the hydrophilic and lipophilic properties of the drug so that the drug permeates the membrane well and blood perfusion rate becomes the overall rate-limiting step for absorption, or by inhibiting drug biotransformation in the gut and/or by inhibiting active back transport systems in the gut that decrease the net transport of drugs across the gut membrane into the blood stream. In either case, the composition responsible for increased drug bioavailability is the orotate salt of the pharmaceutical agent. For reasons that are not immediately apparent, it has been discovered that conversion of a water-insoluble pharmaceutical agent into an orotate salts provides a method for increasing the bioavailability of an orally administered pharmaceutical agent to a mammal in need of treatment in sufficient amount to provided integrated systemic concentrations over time of the orotate agent over the agent without conversion to an orotate salt.

Changes in the integrated systemic concentrations over-time are indicated by area under the curve (AUC) or $C_{max}$, both parameters well known in the art. AUC is a determination of the Area Under the Curve plotting the serum or plasma concentration of drug along the ordinate (Y-axis) against time along the abscissa (X-axis). Generally, the values for the AUC represent drug concentrations over time in units of mass—time/volume. When efficacy of the orotate salt of the agent is being measured, the amount and form of the active drug administered should be the same in both the administration of the drugs as orotate and the administration of the drug alone.

The present invention provides methods wherein a composition provides an increase in bioavailability of the orotate salt of the pharmaceutical agent as measured by AUC of at least 25% relative to dosing of the pharmaceutical agent. The present invention also provides methods wherein the composition provides an increase in bioavailability of the orotate salt of the pharmaceutical agent as measured by AUC of at least 50% relative to dosing of the pharmaceutical agent. The present invention further provides methods wherein said composition provides an increase in bioavailability of the orotate salt of the pharmaceutical agent as measured by AUC of at least 100% relative to dosing of the pharmaceutical agent.

The invention provides a composition that increases the bioavailability of the orotate salt of the pharmaceutical agent as measured by Cmax of at least 50% relative to dosing of the pharmaceutical agent. The invention also provides said composition that increases the bioavailability of the orotate salt of the pharmaceutical agent as measured by Cmax of at least 100% relative to dosing of the pharmaceutical agent. The invention further provides said composition which provides an increase in bioavailability of the orotate salt of the pharmaceutical agent as measured by Cmax of at least 200% relative to dosing of the pharmaceutical agent. Systemic drug concentrations are measured using standard biochemical drug measurement techniques (Simmons et al., Anal Lett. 39: 2009-2021 (1997).

Characteristics of Drugs Used as Orotate Salts

The word "drug" as used herein is defined as a chemical intended for use in the treatment or prevention of disease. Drugs include synthetic and naturally occurring bioaffecting substances as well as recognized pharmaceuticals, such as those listed in "The Physician desk Reference," 56th ed, pages 101-133 (or an updated edition). These references are incorporated by reference herein. The present invention can be used with drugs consisting of charged, uncharged, hydrophilic, zwitter-ionic, or hydrophobic species, as well as any combinations of these physical characteristics. A hydrophobic drug is defined as a drug which in its non-ionized form is more soluble in lipid or fat than in water. A preferred class of hydrophobic drugs is those drugs that are more soluble in octanol than in water.

Compounds or drugs from a number of classes of compounds can be converted to orotate salts and administered orally as orotate salts. The compound or drug can be for example, but is not limited to the following classes: acetanilide, adriamycin, aminoacridine, aminoimidazole, aminoquinoline, anilide, anthracycline antibiotic, antiestrogen, benzazepine, benzhydryl compound, benzodiazpine, benzofuran, cannabinoid, cephalosporine, cisplatin, colchicines, cyclic peptide, cyclophosphamide, dibenzazepine, digitalis glycoside, dihydropyridine, doxorubicin, epiphodophyllotoxin, epirubicin, ergoline, ergot alkaloid, fluorouracil, imidazole, isoquinoline, macrolide, methotrexate, mitomycin, naphthalene, nitrogen mustard, opioid, oxazine, oxazole, paclitaxel, phenothiazine, phenylalkamine, phenylpiperidine, piperazine, piperidine, polycyclic aromatic hydrocarbon, pyridine, pyridine, pyrimidine, pyrrolidine, pyrrolidinone, quinazoline, quinoline, quinine, rauwolfa alkaloid, retinoid, salicylate, steroid, stilbene, sulfone, sulfonylurea, tamoxifen, taxol, taxotere, triazole, tropane, vincristine or vinca alkaloid.

Bioavailability of a drug following oral dosing is the extent to which or rate at which the active moiety of the drug or metabolite enters systemic circulation, thereby gaining access to the site of action. The physicochemical properties of a drug govern its absorptive potential, but the properties of the dosage form which partly depend on its design and manufacture, can largely determine drug bioavailability. Differences in bioavailability among formulations of a given drug can have clinical significance. The concept of equivalence among drug products is important in making clinical decisions.

"Chemical equivalence" refers to drug products that contain the same compound in the same amount and that meet current official standards. However, inactive ingredients in drug products may differ.

"Bioequivalence" refers to chemical equivalents that, when administered to the same person in the same dosage regimen, result in equivalent concentrations of drug in blood and tissues.

"Therapeutic equivalence" refers to drug products that, when administered to the same person in the same dosage regimen, provide essentially the same therapeutic effect or toxicity. Bioequivalent products are expected to be therapeutically equivalent. Sometimes therapeutic equivalence may be achieved despite differences in bioavailability, for example when the therapeutic index is wide (ratio of maximum tolerated dose to the minimum effective dose).

"Absorption" rate is important because even when a drug is absorbed completely, it may be absorbed too slowly to produce a therapeutic blood level quickly enough or so rapidly that toxicity results from high drug concentrations given to achieve the therapeutic level after each dose.

Figure 2:
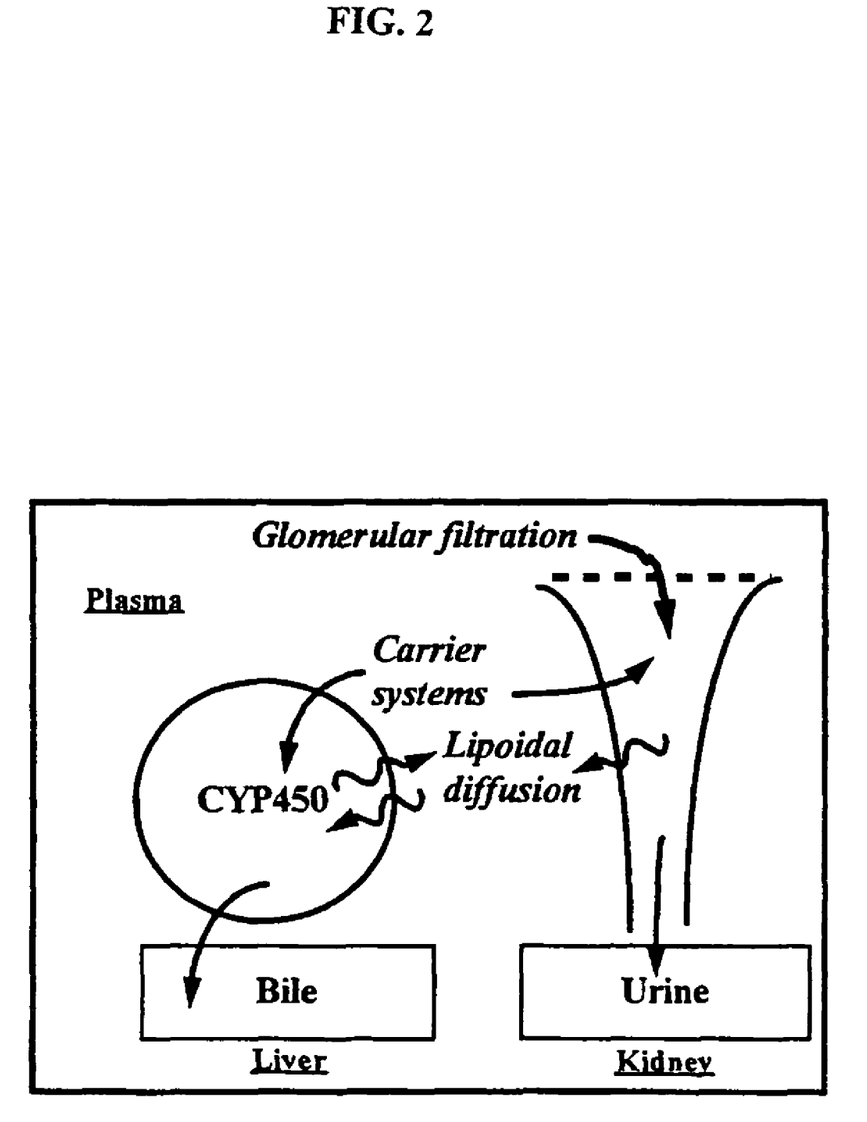
FIG. 2 is a schematic illustrating the interplay of hepatic and renal clearance processes.

"Clearance" of drug occurs by perfusion of blood to the organs of extraction. "Extraction" refers to the proportion of drug presented to the organ which is removed irreversibly (excreted) or altered to a different chemical form (metabolism). Clearance (CL) is therefore calculated as the product of the flow of blood through the organ and proportion of the drug extracted by the organ. FIG. 2 is a schematic illustrating the interplay of hepatic and renal clearance.

Clearance of drug normally occurs from the liver and kidneys and it is assumed that only free and not protein bound, drug is available for clearance. For hepatic clearance, passive diffusion through the lipid core of the hepatocyte membranes, available to lipophilic drugs, is augmented by sinusoidal carrier systems particularly for ionized molecules (anionic and cationic) of molecular weights of above 400. Likewise other transporters on the canalicular face transport drugs or their metabolites into bile. This system has two separate processes, hepatic uptake and billiary excretion. With small sized lipophilic drugs that readily traverse membranes hepatic uptake is not a major factor, but with higher molecular weight compounds (above 500) and those containing considerable H-bonding hepatic uptake can become the key clearance process, even if metabolism occurs subsequent to this. Administration of ketoconazole, a potent cytochrome p450 inhibitor decreases the metabolism of some compounds, for example CAI. Desai A A et al, Cancer Chemotherapy Pharmacol 54: 377-384, 2004. Ketoconazole was reported to increase the bioavailability of CAI but failed to change the toxicity associate with CAI.

The present invention a method to increase in clearance of the orotate salt of the pharmaceutical agent as measured by pharmacokinetic studies at least 25% relative to dosing of the pharmaceutical agent. The invention also provides a method to increase in clearance of the orotate salt of the pharmaceutical agent as measured by pharmacokinetic studies of at least 50% relative to dosing of the pharmaceutical agent. The invention further provides a method to increase in clearance of the orotate salt of the pharmaceutical agent as measured by pharmacokinetic studies of at least 100% relative to dosing of the pharmaceutical agent.

The present invention a composition that increases clearance of the orotate salt of the pharmaceutical agent as measured by pharmacokinetic studies in of at least 50% relative to dosing of the pharmaceutical agent. It also provides a composition that increases in clearance of the orotate salt of the pharmaceutical agent as measured by pharmacokinetic studies of at least 100% relative to dosing of the pharmaceutical agent. It further provides said composition that increases inclearance of the orotate salt of the pharmaceutical agent as measured by pharmacokinetic studies of at least 200% relative to dosing of the pharmaceutical agent.

Causes of Low Bioavailability

When a drug rapidly dissolves and readily crosses the intestinal membranes, absorption tends to be complete, but absorption of orally administered drugs is not always complete. Before reaching the vena cava, a drug must move down the gastrointestinal tract and pass through the gut wall and liver, common sites of drug metabolism. Thus a drug may be metabolized during first-pass metabolism before it can be measured in the systemic circulation. Many drugs have low oral bioavailability because of expensive first-pass metabolism.

Low bioavailability is most common with oral dosage forms of poorly water-soluble, slowly absorbed drugs. More factors can affect bioavailability when absorption is slow or incomplete than when it is rapid and complete. That is, slow or incomplete absorption leads to variable therapeutic responses. Slow absorption in the gastrointestinal tract also leads to increased acute and delayed-phase chemotherapy induced nausea and vomiting.

Insufficient time in the gastrointestinal tract is a common cause of low bioavailability. Ingested drug is exposed to the entire gastrointestinal tract for no more than one to two days and to the small intestine for only 2 to 4 hours. If the drug does not dissolve readily or cannot penetrate the epithelial membrane (e.g., if it is highly ionized and polar), time at the absorption site may be insufficient. In such cases, bioavailability tends to be highly variable as well as low. Age, sex, activity, genetic phenotype, stress, disease or previous gastrointestinal surgery can affect drug bioavailability.

Reactions that compete with absorption can reduce bioavailability. They include complex formation, hydrolysis by gastric acid or digestive enzymes, conjugation in the gut wall, absorption of other drugs and metabolism by luminal micro flora.

Assessment of bioavailability from plasma concentration-time data usually involves determining maximum peak concentration, the time at which maximum peak plasma drug concentration occurs, and the area under the plasma concentration time curve (AUC). The plasma drug concentration increases with the extent of absorption. The peak is reached when the drug elimination rate equals absorption rate. AUC is the most reliable measure of bioavailability. It is directly proportional to the total amount of unchanged drug that reaches the systemic circulation.

Drug products may be considered bioequivalent in extent and rate of absorption if their plasma level curves are essentially super imposable. Drug products that have similar AUCs but differently shaped plasma level curves are equivalent in extent but differ in their absorption rate-time profiles.

Absorption occurs by one of three methods, either passive diffusion, active transport or facilitated active transport. Passive diffusion is simply the passage of molecules across the mucosal barrier until the concentration of molecules reaches osmotic balance on both sides of the membrane. In active transport the molecule is actively pumped across the mucosa. In facilitated transport, a carrier generally a protein, is required to convey the molecule across the membrane for absorption.

Methods of Enhancing Effectiveness and Reducing Side Effects of an Agent by Converting it to an Orotate Salt.

The present invention describes the method of increasing the oral bioavailability of pharmaceutical agents that are poorly absorbed from the gastrointestinal tract by converting them into orotate salts. The invention also describes improved effectiveness of CAI orotate in inhibiting tumor growth compared with CAI given directly. The invention describes increased clearance of the drug as an orotate salt than when given directly. Thus, the orotate salts of the drugs can be dosed at lower doses to provide the efficacy benefits of a higher dose, while reducing the drugs' toxic effects at lower doses and reduce acute and delayed-phase chemotherapy-induced nausea and vomiting. Therefore, an especially useful formulation of the orotate salt of the pharmaceutical agent can provide rapid onset and consistent action using a lower dose and reduce drug interactions and side-effects because of consistent delivery.

Figure 3:
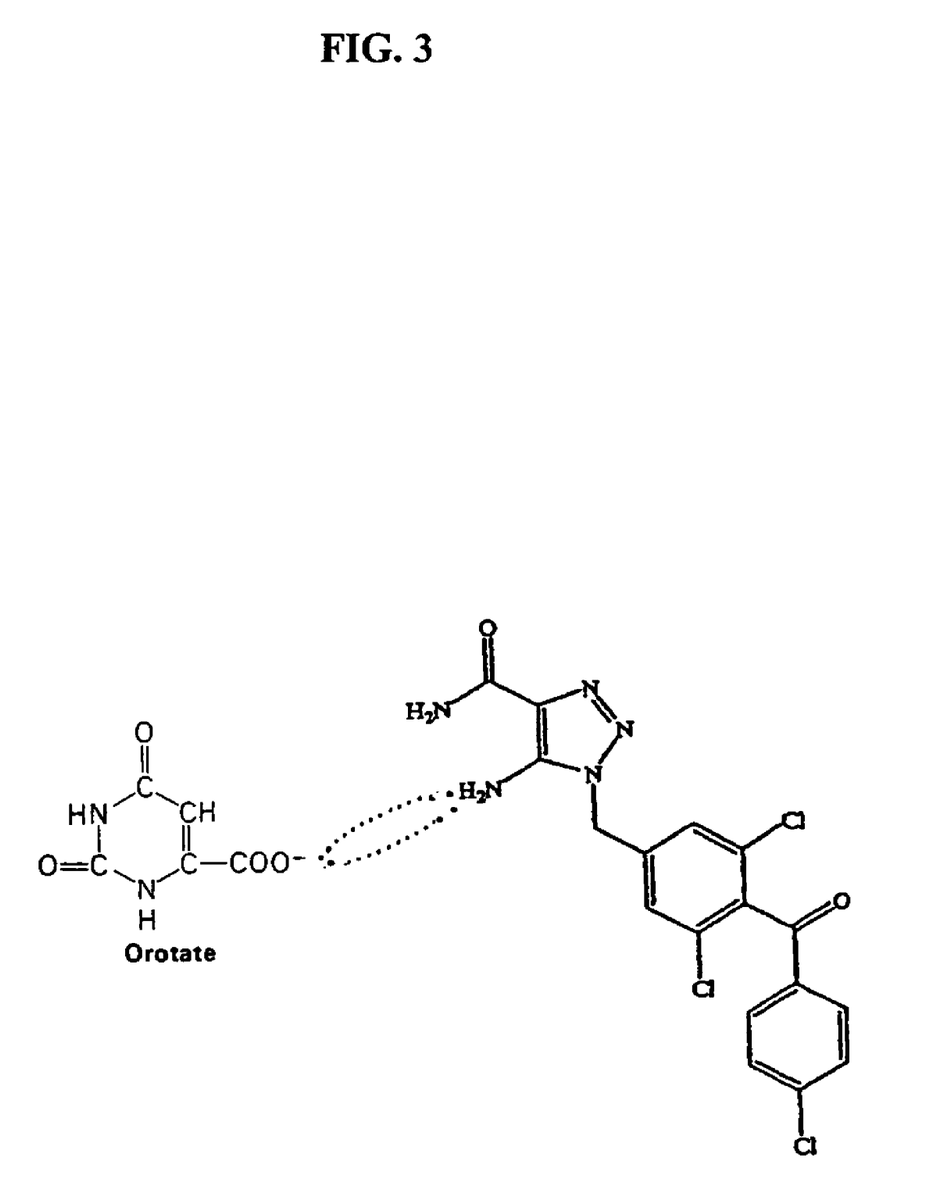
FIG. 3 depicts the formula for carboxyamidotriazole or 5 amino 1,2,3-triazole and orotic acid. Orotic acid, an organic acid, is bonded to the charged portion of the amino group on CAI.

Orotic acid, a free pyrimidine is important in the synthesis of uridylate (UPP) a major pyrimidine nucleotide. Pyrimidines play a central role in cellular regulation and metabolism. They are substrates for DNA/RNA biosynthesis, regulators of the biosynthesis of some amino acids, and cofactors in the biosynthesis of phospholipids, glycolipids, sugars and polysaccharides. The classical de novo pyrimidine biosynthetic pathway ends with the synthesis of UMP. Biochemistry, ed Lubert Stryer, ed, W.H. Freeman & Co NY, $4^{th}$ ed, 739-762 (1995). It has also been reported that 5-Fluorouracil is toxic to the liver, as measured by incorporation in the acid soluble fraction, RNA and DNA in normal tissues in the liver of rats. Orotic acid administration decreased the incorporation into the liver and intestinal RNA, thus suggesting that it reduces 5-FU induced toxicity in the liver. El Hag IA et al, In vivo 1: 309-312 (1987). FIG. 3 describes the formula for Orotic acid and CAI orotate. The present invention provides drug orotate salts that under go dissolution to release the drug as a charged molecule and free orotic acid, which in turn reduces drug-induced liver toxicity.

The present invention provides methods and compositions to increase the effectiveness of a pharmaceutical agent by converting said pharmaceutical agent to an orotate salt composition and, administering said orotate salt to a subject in need thereof, said pharmaceutical agent selected from the group of consisting of acetanilide, adriamycin, aminoacridine, aminoimidazole, aminoquinoline, anilide, anthracycline antibiotic, antiestrogen, benzazepine, benzhydryl compound, benzodiazpine, benzofuran, cannabinoid, cephalosporine, colchicines, cyclic peptide, cyclophosphamide, dibenzazepine, digitalis glycoside, dihydropyridine, doxorubicin, epiphodophyllotoxin, epirubicin, ergoline, ergot alkaloid, fluorouracil, imidazole, isoquinoline, macrolide, methotrexate, naphthalene, nitrogen mustard, opioid, oxazine, oxazole, paclitaxel, phenothiazine, phenylalkamine, phenylpiperidine, piperazine, piperidine, polycyclic aromatic hydrocarbon, pyridine, pyridine, pyrimidine, pyrrolidine, pyrrolidinone, quinazoline, quinoline, quinine, rauwolfa alkaloid, retinoid, salicylate, steroid, stilbene, sulfone, sulfonylurea, tamoxifen, taxol, taxotere, triazole, tropane, vinblastine or vinca alkaloid.

The invention provides methods and compositions to increase effectiveness of the orotate salt of the pharmaceutical agent as measured by inhibition of tumor growth of at least 25% relative to dosing of the pharmaceutical agent. It also provides methods and compositions to increase effectiveness of the orotate salt of the pharmaceutical agent as measured by inhibition of tumor growth of at least 50% relative to dosing of the pharmaceutical agent. It provides methods and compositions to increase effectiveness of the orotate salt of the pharmaceutical agent as measured by inhibition of tumor growth of at least 100% relative to dosing of the pharmaceutical agent.

The invention provides methods and compositions to increase effectiveness of the orotate salt of the pharmaceutical agent as measured by its stable concentration for a therapeutic end point of at least 25% relative to dosing of the pharmaceutical agent. It also provides methods and compositions to increase effectiveness of the orotate salt of the pharmaceutical agent as measured by its stable concentration for therapeutic end point of at least 50% relative to dosing of the pharmaceutical agent. It provides methods and compositions to increase effectiveness of the orotate salt of the pharmaceutical agent as measured by its stable concentration for therapeutic end point of at least 100% relative to dosing of the pharmaceutical agent.

6. EXAMPLES

Example 1

Chemical Synthesis of CAI Orotate

FIG. 3 depicts the formula for CAI orotate. The orotate salt was prepared using the procedure described in U.S. Pat. No. 5,861,406, with the reaction solution of water/methanol (1:4 volume) replaced by N,N-dimethyl acetamide. 2 grams of CAI and 0.87 grams of orotic acid were added in N,N-dimethyl acetamide and heated to boiling for 15 mins. The resulting solution was filtered. A white precipitate was formed upon cooling and drying. The molecular weight of CAI is 425. The molecular weight of CAI orotate is 581.

Example 2

Pharmacokinetic Assay for Evaluation of Oral Absorption and Bioavailabiliy of CAI Orotate Male Sprague Dawley rats were fasted overnight then dosed by oral gavage at CAI 100 mg/kg and CAI orotate 137 mg/kg body weight. Blood samples were collected into tubes containing EDTA at various intervals including 30 min, 1 hr, 2, 4, 16 and 48 hrs. The plasma was separated and analyzed for CAI. PK data analysis was carried out using PK SolutionsPharmakokinetic Software Inc, Montrose Colo.

Figure 4:
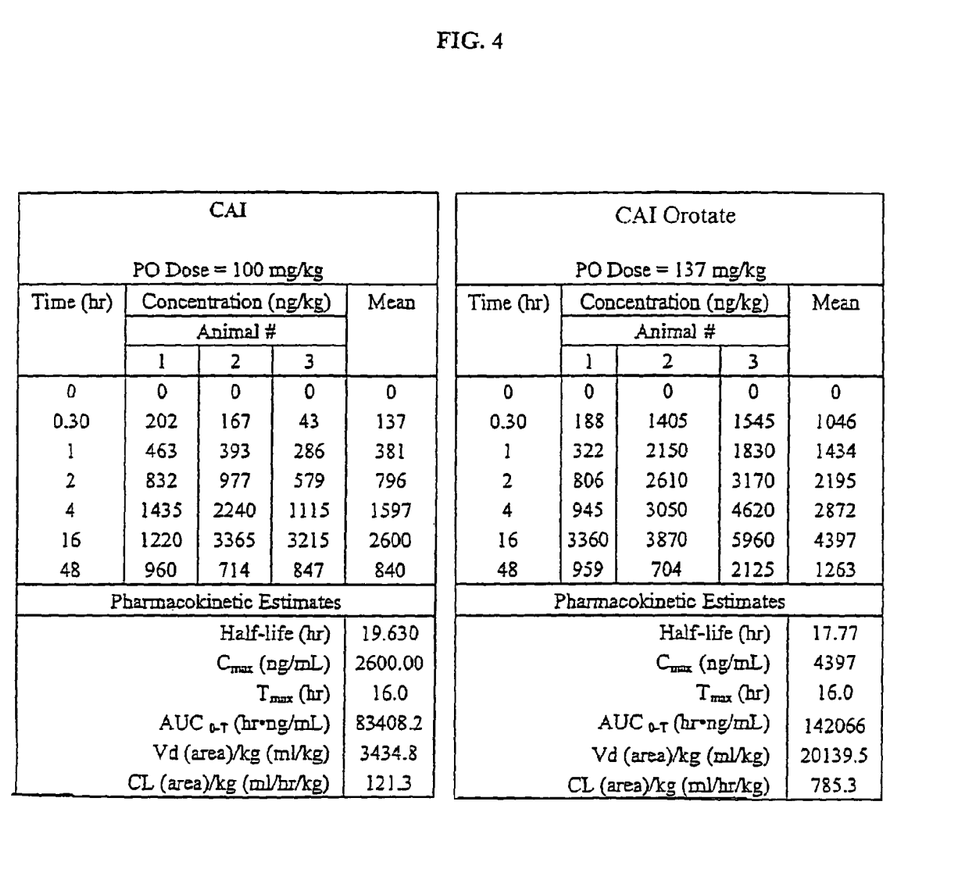
FIG. 4 provides the results for oral bioavailability for CAI or CAI orotate in rats.

Data are shown in FIG. 4. The purpose of the present study was to compare the pharmacokinetic profiles of CAI and CAI orotate. CAI showed a PK profile similar to that previously reported with a half life of approximately 19 hours and a Tmax of about 16 hrs.

The CAI salt has a plasma half life of about 18 hrs. While the Tmax was similar for both compounds (16 hrs) the Cmax was nearly double for CAI orotate. Higher plasma concentration appeared earlier in the plasma for the CAI orotate compared to CAI. Area under curve (AUC) was higher for CAI orotate and these data together suggest that CAI orotate is getting through the gastrointestinal tract more faster than CAI.

Example 3

Increasing the Therapeutic Efficacy of an Agent by Conversion to Orotate Salt

The purpose of the experiment was to evaluate the antitumor efficacy of CAI and CAI orotate against subcutaneously implanted LOX IMVI human melanoma xenografts in female athymic NCr-nu mice.

Figure 5:
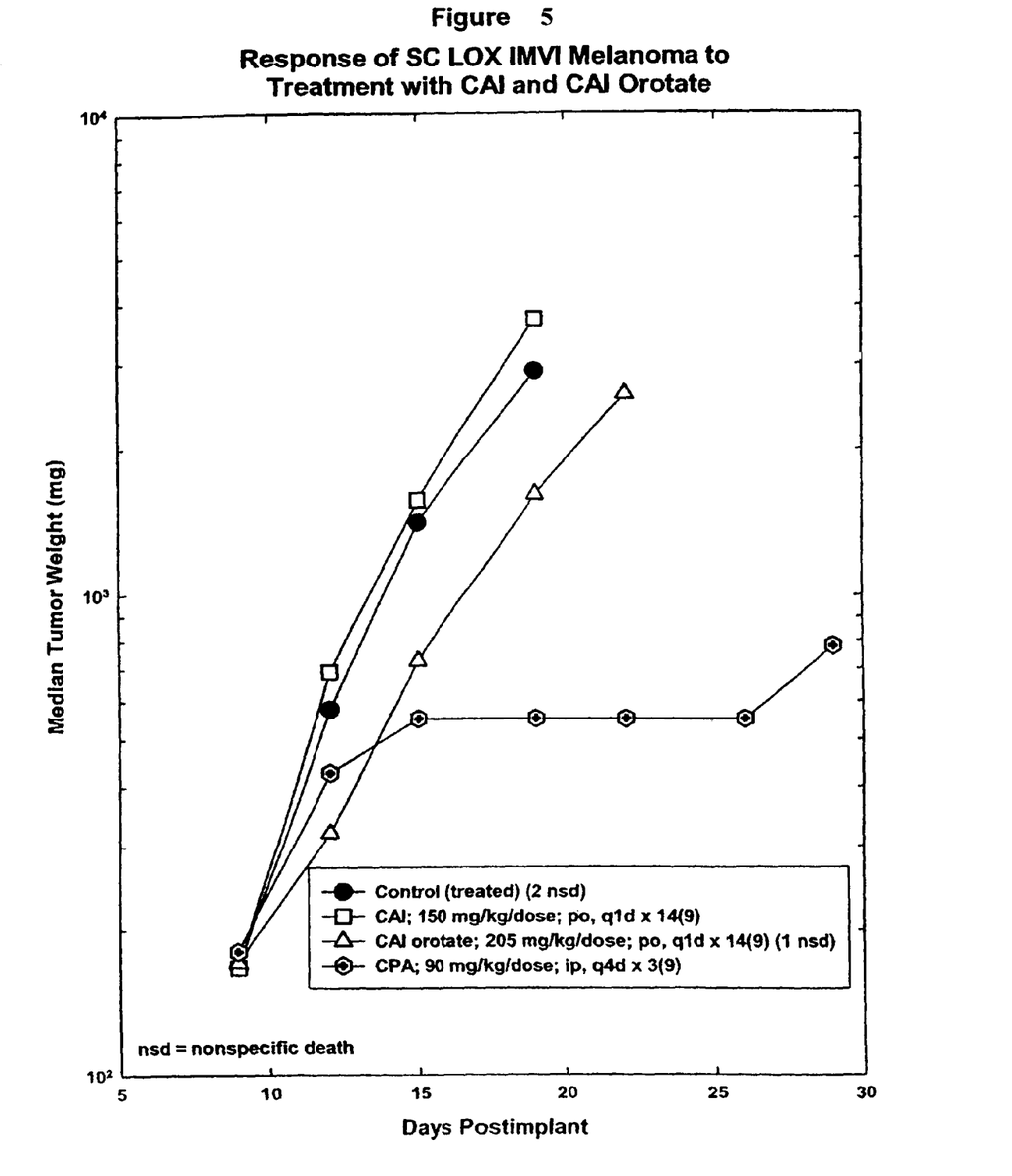
FIG. 5 shows results obtained show that oral administration of CAI orotate once daily for 14 days at a dosage of 205 mg/kg/dose resulted in inhibition of the growth of the implanted LOX IMVI human melanoma xenografts significantly (p-0.0487) compared to the CAI treated group.

FIG. 5 shows the results. Results obtained indicate that LOXIMVI human melanoma xenografts are sensitive to the treatment of cyclophosphamide—a control drug used to compare CAI and CAI orotate. Results obtained show that oral administration of CAI orotate once daily for 14 days at a dosage of 205 mg/kg/dose resulted in inhibition of the growth of the implanted LOX IMVI human melanoma xenografts significantly (p-0.0487) compared to the CAI treated group.

Example 4

Reducing the Side Effects of an Agent by Conversion to Orotate Salt

CAI and CAI orotate were evaluated compared with Cisplatin induced emesis in the ferret. The ferret is very sensitive to emetic agents. The emetic effect of cytotoxic agents such as cisplatin/doxorubicin and cyclophosphamide can be shown in the ferret. CAI, CAI orotate and cisplatin were studied in ferrets according to the procedure described in Oncology 53: Suppl 1: 8-17, (1996). Results obtained indicate that neither CAI or CAI orotate appeared to have acute toxic effects that were seen in dogs for CAI. The ferrets tolerated a dose of 250 mg/kg CAI or 343 mg/kg PO with no obvious effects other than mild retching over a 5 hour observation period. CAI orotate appeared to have less potential for producing pre-emetic behavior and retching than CAI.

Example 5

General Example

A number of drugs have very low aqueous solubility, mainly due to very high lipophilicity, but also due to lack of ionizable centres. These drugs are erratically and incompletely absorbed due to their inability to dissolve in the gastrointestinal tract following oral administration, for example, ketoconozaole, phenyloin and tiramterene. Poor dissolution is responsible for both intra- and inter-patient variability in drug absorption and therefore presents a major problem in drug design. However, for such drugs, if the drug has an ionizable centre then solubility can be improved by salt formation.

Figure 6:
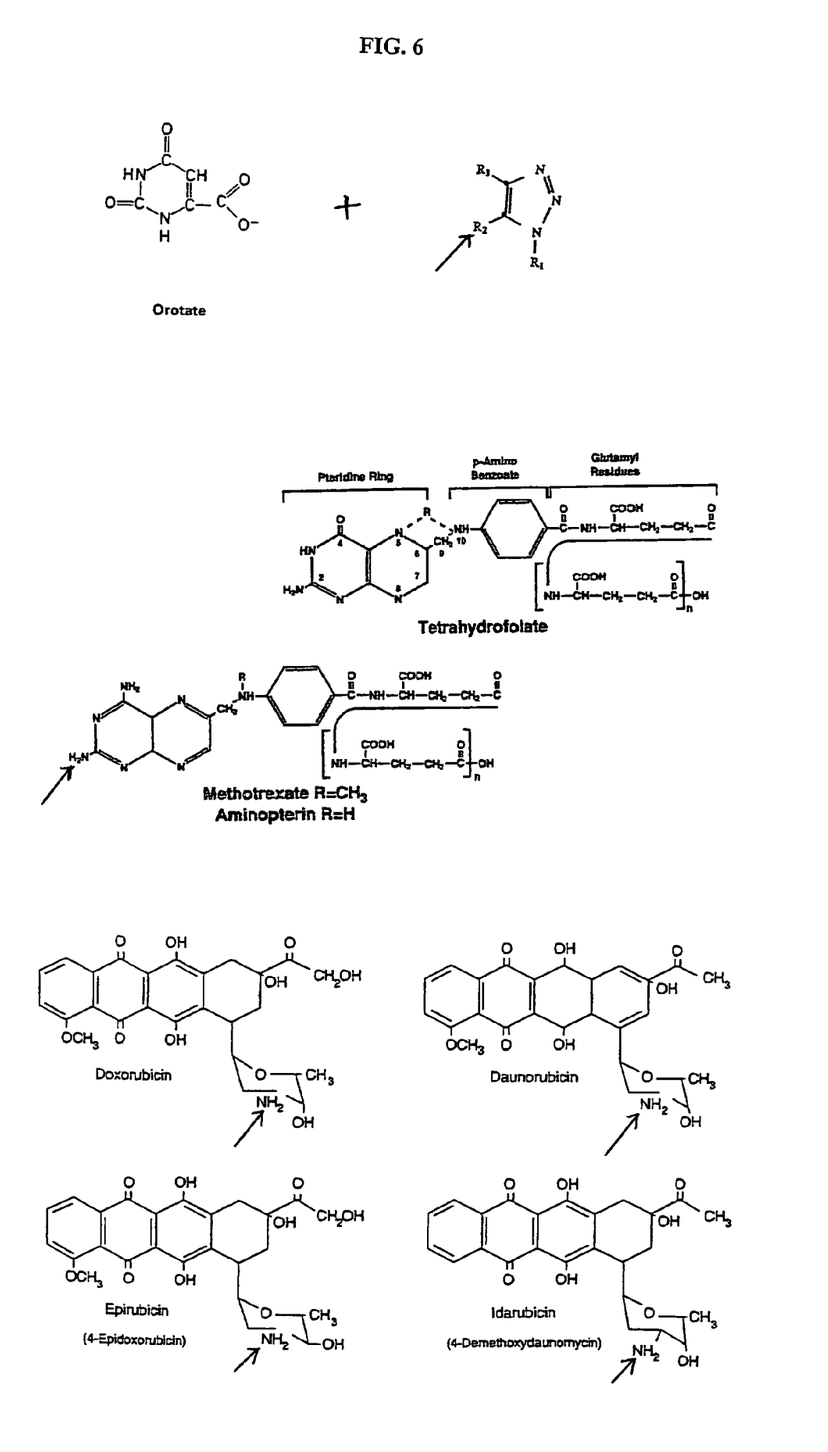
FIG. 6 shows lead compounds having a charged center which is suitable to form orotate salts to achieve increased oral bioavailability of the compound.

For example, FIG. 6 shows some lead compounds currently in use that are suitable to convert to orotate salts to improve their oral bioavailability including but not limited to, doxorubicin and methotrexate.

The present invention is not to be limited in scope by the embodiment disclosed in the example which is intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Those skilled in the art will recognize, or be able to ascertain using no more than routine experimentation, any equivalents to the specific embodiments of the invention described herein. Such equivalents are intended to be encompassed by the claims.

What is claimed is:

1. A method of increasing the absorption and bioavailability of a pharmaceutical compound having an ionizable center capable of reacting with orotic acid, by converting said pharmaceutical compound to an orotate salt and, administering orally said orotate salt to a mammal to increase the absorption and bioavailability of said pharmaceutical compound, wherein said pharmaceutical compound is selected from the group consisting of acetanilide, anilide, anthracycline antibiotic, benzodiazepine, cephalosporine, colchicines, cyclophosphamide, digitalis glycoside, dihydropyridine, epiphodophyllotoxin, epirubicin, ergot alkaloid, fluorouracil, macrolide, nitrogen mustard, phenothiazine, phenylpiperidine, pyrimidine, retinoid, sulfonylurea, tamoxifen, vinblastine or vinca alkaloid.

2. The method according to claim 1 wherein said orotate salt provides an increase in bioavailability of the pharmaceutical compound, such bioavailability being measured by AUC of at least 25% relative to dosing of the pharmaceutical compound.

3. The method according to claim 1 wherein said orotate salt provides an increase in bioavailability of the pharmaceutical compound, such bioavailability being measured by AUC of at least 50% drug relative to dosing of the pharmaceutical compound.

4. The method according to claim 1 wherein said orotate salt provides an increase in bioavailability of the pharmaceutical compound, such bioavailability being measured by AUC of at least 100% relative to dosing of the pharmaceutical compound.

5. The method according to claim 1 wherein said orotate salt provides an increase in bioavailability of the pharmaceutical compound, such bioavailability being measured by Cmax of at least 50% relative to dosing of the pharmaceutical compound.

6. The method according to claim 1 wherein said orotate salt provides an increase in bioavailability of the pharmaceutical compound, such bioavailability being measured by Cmax of at least 100% relative to dosing of the pharmaceutical compound.

7. The method according to claim 1 wherein said orotate salt provides an increase in bioavailability of the pharmaceutical compound, such bioavailability being measured by Cmax of at least 200% relative to dosing of the pharmaceutical compound.

8. The method according to claim 1 wherein said increase in bioavailability of the pharmaceutical compound is measured in blood plasma.

9. A method of increasing the clearance (CL) of a pharmaceutical compound having an ionizable center capable of reacting with orotic acid by converting said pharmaceutical compound to an orotate salt and, orally administering said orotate salt to a mammal to improve clearance of said pharmaceutical compound, wherein said pharmaceutical compound is selected from the group of consisting of acetanilide, anilide, anthracycline antibiotic, benzodiazepine, cephalosporine, colchicines, cyclophosphamide, digitalis glycoside, dihydropyridine, epiphodophyllotoxin, epirubicin, ergot alkaloid, fluorouracil, macrolide, nitrogen mustard, phenothiazine, phenylpiperidine, pyrimidine, retinoid, sulfonylurea, tamoxifen, vinblastine or vinca alkaloid.

10. The method according to claim 9 wherein said orotate salt provides an increase in clearance of the pharmaceutical compound, such clearance being measured by CL of at least 25% relative to dosing of the pharmaceutical compound.

11. The method according to claim 9 wherein said orotate salt provides an increase in clearance of the pharmaceutical compound, such clearance being measured by CL of at least 50% relative to dosing of the pharmaceutical compound.

12. The method according to claim 9 wherein said orotate salt provides an increase in clearance of the pharmaceutical compound, such clearance being measured by CL of at least 100% relative to dosing of the pharmaceutical compound.

13. The method according to claim 9 wherein said orotate salt provides an increase in clearance of the pharmaceutical compound, such clearance being measured by renal excretion of at least 50% relative to dosing of the pharmaceutical compound.

14. The method according to claim 9 wherein said orotate salt provides an increase in clearance of the pharmaceutical compound, such clearance being measured by renal excretion of at least 100% relative to dosing of the pharmaceutical compound.

15. The method according to claim 9 wherein said orotate salt provides an increase in clearance of the pharmaceutical compound, such clearance being measured by renal excretion of at least 200% relative to dosing of the pharmaceutical compound.

16. The method according to claim 9 wherein said increase in clearance of the pharmaceutical compound is measured in blood plasma.

17. A method of reducing toxicity of a pharmaceutical compound having an ionizable center capable of reacting with orotic acid by converting said pharmaceutical compound to an orotate salt and, administering said orotate salt to a mammal to reduce toxicity of said pharmaceutical compound, wherein said pharmaceutical compound is selected from the group of consisting of acetanilide, anilide, anthracycline antibiotic, benzodiazepine, cephalosporine, colchicines, cyclophosphamide, digitalis glycoside, dihydropyridine, epiphodophyllotoxin, epirubicin, ergot alkaloid, fluorouracil, macrolide, nitrogen mustard, phenothiazine, phenylpiperidine, pyrimidine, retinoid, sulfonylurea, tamoxifen, vinblastine or vinca alkaloid.

18. The method according to claim 17 wherein said orotate salt reduces toxicity of the pharmaceutical compound, such toxicity being measured by recording symptoms emesis of at least 25% relative to dosing of the pharmaceutical compound.

19. The method according to claim 17 wherein said orotate salt reduces toxicity of the pharmaceutical compound, such toxicity being measured by recording symptoms of emesis of at least 50% relative to dosing of the pharmaceutical compound.

20. The method according to claim 17 wherein said orotate salt reduces toxicity of the pharmaceutical compound, such toxicity being measured by recording symptoms emesis of at least 100% relative to dosing of the pharmaceutical compound.

21. The method according to claim 17 wherein said orotate salt reduces toxicity of the pharmaceutical compound, such toxicity being measured by hepatic toxicity of at least 50% relative to dosing of the pharmaceutical compound.

22. The method according to claim 17 wherein said orotate salt reduces toxicity of the pharmaceutical compound, such toxicity being measured by hepatic toxicity of at least 100% relative to dosing of the pharmaceutical compound.

23. The method according to claim 17 wherein said orotate salt reduces toxicity of the pharmaceutical compound, such toxicity being measured by hepatic toxicity of at least 200% relative to dosing of the pharmaceutical compound.

24. A method of increasing the effectiveness of a pharmaceutical compound having an ionizable center capable of reacting with orotic acid by converting said pharmaceutical compound to an orotate salt and, administering said orotate salt to a mammal to improve effectiveness of said pharmaceutical compound, wherein said pharmaceutical compound is selected from the group of consisting of acetanilide, anilide, anthracycline antibiotic, benzodiazepine, cephalosporine, colchicines, cyclophosphamide, digitalis glycoside, dihydropyridine, epiphodophyllotoxin, epirubicin, ergot alkaloid, fluorouracil, macrolide, nitrogen mustard, phenothiazine, phenylpiperidine, pyrimidine, retinoid, sulfonylurea, triazole, vinblastine or vinca alkaloid.

25. The method according to claim 24 wherein said orotate salt increases the effectiveness of the pharmaceutical compound such effectiveness being measured by inhibition of tumor growth of at least 100% relative to dosing of the pharmaceutical compound.

26. The method according to claim 24 wherein said orotate salt increases the effectiveness and provides stable concentrations of pharmaceutical compound such concentration being measured by stable blood concentrations of at least 50% relative to dosing of the pharmaceutical compound.

27. The method according to claim 24 wherein said orotate salt increases the effectiveness and provides stable concentrations of pharmaceutical compound such effectiveness being measured by stable blood concentrations of at least 100% relative to dosing of the pharmaceutical compound.

28. The method according to claim 24 wherein said orotate salt increases the effectiveness and provides stable concentrations of the pharmaceutical compound such effectiveness being measured by stable blood concentrations of at least 200% relative to dosing of the pharmaceutical compound.

29. The method according to claim 24 wherein said increase effectiveness of the pharmaceutical compound is measured in blood plasma.

* * * * *